United States Patent
Wang et al.

(10) Patent No.: US 7,128,956 B2
(45) Date of Patent: Oct. 31, 2006

(54) CATHETER HAVING IMPROVED CURVE RETENTION

(75) Inventors: Bruce Yiqun Wang, Maple Grove, MN (US); John Chen, Plymouth, MN (US); Lixiao Wang, Maple Grove, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/983,470

(22) Filed: Nov. 8, 2004

(65) Prior Publication Data

US 2005/0064124 A1 Mar. 24, 2005

Related U.S. Application Data

(63) Continuation of application No. 10/020,521, filed on Dec. 14, 2001, now abandoned.

(51) Int. Cl.
| | |
|---|---|
| *B32B 1/08* | (2006.01) |
| *F16L 11/04* | (2006.01) |
| *F16L 11/08* | (2006.01) |
| *A61M 25/04* | (2006.01) |
| *B29D 23/00* | (2006.01) |
| *A61M 25/09* | (2006.01) |
| *A61M 25/10* | (2006.01) |

(52) U.S. Cl. .................. 428/36.9; 428/35.7; 428/36.91; 604/264; 604/523; 604/525; 604/528; 604/530; 604/532; 138/118; 138/DIG. 8

(58) Field of Classification Search ................ 604/264, 604/523, 525, 528, 530, 532; 428/36.9, 35.7, 428/36.91; 138/118, DIG. 8

See application file for complete search history.

(56) References Cited

U.S. PATENT DOCUMENTS 4,464,176 A 8/1984 Wijayarathna (Continued)

FOREIGN PATENT DOCUMENTS

EP 0 628 586 A1 12/1994

(Continued)

OTHER PUBLICATIONS

Jansen, "Nucleating Agents for Partly Crystalline Polymers," dated on or before Sep. 20, 2001, pp. 863-875.

*Primary Examiner*—Nasser Ahmad
*Assistant Examiner*—Chris Bruenjes
(74) *Attorney, Agent, or Firm*—Crompton, Seager & Tufte, LLC (57) ABSTRACT

The present invention provides a polymeric treatment for curved regions in shaft assemblies that increases curve retention without affecting the flexibility within these regions. More specifically, the present invention modifies the underlying crystalline morphology of a polymer in order to decrease crystal fracturing. In particular, the present invention treats polymeric materials suitable for catheter construction with a nucleating agent.

24 Claims, 3 Drawing Sheets

U.S. PATENT DOCUMENTS

| | | | |
|---|---|---|---|
| 4,817,613 A | 4/1989 | Jaraczewski et al. | |
| 4,886,506 A | 12/1989 | Lovgren et al. | |
| 4,898,591 A | 2/1990 | Jang et al. | |
| 4,931,538 A | 6/1990 | Yoshifumi et al. | |
| 5,047,045 A | 9/1991 | Arney et al. | |
| 5,114,402 A | 5/1992 | McCoy | |
| 5,156,594 A | 10/1992 | Keith | |
| 5,290,229 A | 3/1994 | Paskar | |
| 5,316,706 A | 5/1994 | Muni et al. | |
| 5,335,410 A | 8/1994 | Burnham | |
| 5,340,884 A | 8/1994 | Mills et al. | |
| 5,477,856 A | 12/1995 | Lundquist | |
| 5,516,565 A | 5/1996 | Matsumoto | |
| 5,562,127 A | 10/1996 | Fanselow et al. | |
| 5,599,325 A | 2/1997 | Ju et al. | |
| 5,674,208 A | 10/1997 | Berg et al. | |
| 5,721,023 A | 2/1998 | Ostapchenko | |
| 5,810,867 A | 9/1998 | Zarbatany et al. | |
| 5,836,926 A | 11/1998 | Peterson et al. | |
| 5,885,259 A | 3/1999 | Berg | |
| 5,911,715 A | 6/1999 | Berg et al. | |
| 6,001,085 A | 12/1999 | Lurie et al. | |
| 6,030,360 A | 2/2000 | Biggs | |
| 6,030,405 A | 2/2000 | Zarbatany et al. | |
| 6,042,578 A | 3/2000 | Dinh et al. | |
| 6,146,355 A | 11/2000 | Biggs | |
| 6,156,842 A | 12/2000 | Hoenig et al. | |
| 6,159,187 A | 12/2000 | Park et al. | |
| 6,171,278 B1 | 1/2001 | Wang et al. | |
| 6,171,295 B1 | 1/2001 | Garabedian et al. | |
| 6,176,871 B1 | 1/2001 | Pathak et al. | |
| 6,199,262 B1 * | 3/2001 | Martin | 29/525.15 |
| 6,212,422 B1 | 4/2001 | Berg et al. | |
| 6,217,554 B1 * | 4/2001 | Green | 604/164.01 |
| 6,242,063 B1 | 6/2001 | Ferrera et al. | |
| 6,245,030 B1 | 6/2001 | DuBois et al. | |
| 6,254,949 B1 | 7/2001 | Gluck et al. | |
| 6,325,790 B1 * | 12/2001 | Trotta | 604/523 |
| 6,358,450 B1 | 3/2002 | Sun | |
| 6,465,067 B1 | 10/2002 | Wang et al. | |
| 6,524,296 B1 | 2/2003 | Beals | |
| 6,562,049 B1 * | 5/2003 | Norlander et al. | 606/108 |
| 2001/0027310 A1 * | 10/2001 | Parisi et al. | 604/524 |
| 2002/0077606 A1 | 6/2002 | Trotta | |

FOREIGN PATENT DOCUMENTS

| | | |
|---|---|---|
| EP | 1 136 085 A2 | 9/2001 |
| JP | 62-288652 A | 12/1987 |
| WO | WO 00/50105 A2 | 8/2000 |

* cited by examiner

CATHETER HAVING IMPROVED CURVE RETENTION

CROSS-REFERENCE TO RELATED APPLICATIONS

This application is a continuation of U.S. application Ser. No. 10/020,521, filed Dec. 14, 2001, now abandoned which is incorporated herein by reference.

TECHNICAL FIELD

The present invention relates generally to the field of catheter devices having a pre-formed flexible curve along the length of the catheter body. More specifically, the present invention relates to the use of certain polymeric materials, and the treatment of those polymeric materials, to manufacture pre-formed curves that are more flexible and have a greater curve retention.

BACKGROUND OF THE INVENTION

This invention resides in the construction and use of catheters for interventional procedures in such fields as cardiology, neurology, urology and gastroenterology. Design features are incorporated in these catheters to facilitate their use in: (1) the advancement of the catheter through a patient's bodily passages to reach specific sites in vessels or chambers of interest; (2) correct placement of the catheter's distal tip at a targeted site within the patient, and finally (3) holding the catheter at a targeted site while procedures with other devices are completed including while the site moves in response to normal bodily functions such as breathing or a heart beat.

Guide catheters are one type of catheter utilized in these procedures. Guide catheters are relatively large lumen catheters used to guide smaller diameter catheters such as therapeutic, diagnostic or imaging catheters into bodily passages that are curved or branched. More specifically, guide catheters provide a conduit for at least a portion of the path followed by these additional catheters to desired target sites within a patient's vasculature or other body lumen or organ. In order for the catheter to be effective, however, the catheter must be able to traverse the tortuous pathways of a patient's vasculature or other anatomy in a manner as atraumatic as possible.

In order to function efficiently, guide catheters generally have a relatively stiff main body portion and a relatively soft distal portion. The stiff main body portion gives the guide catheter sufficient pushability and torqueability to allow the guide catheter to be inserted percutaneously into an artery, moved and rotated in the vasculature to position the distal end of the catheter at the desired site. However, the distal portion should have sufficient flexibility so that it can track over a guide wire and be maneuvered through a tortuous path to the treatment site. In addition, a soft distal tip at the very end of the catheter should be used to minimize the risk of causing trauma to a blood vessel while the guide catheter is being moved through the vasculature to the proper position.

Thus, to limit insertion time and discomfort to a patient, a catheter must be stiff enough to resist the formation of kinks, while at the same time, the catheter must possess flexibility to be responsive to maneuvering forces when guiding the catheter through the vascular system. In addition to these features, catheters must be designed to reach a targeted site and maintain the position at that site throughout the procedure. Guide catheters typically have preformed bends formed along their distal portion to facilitate both the placement of the distal end of the guide catheter and to the ostium of a particular coronary artery of a patient and to remain stable once in position. Likewise, angiographic catheters, which are used in evaluating the progress of coronary artery disease in patients, generally have a desired distal end curvature configuration to facilitate both the steering of the catheter to a particular artery to be examined and to provide a stable positioning of the catheter's distal portion.

As stated above, improved stabilization of a catheter's position is often achieved through curves or bends imparted to the catheter by the manufacturer. Some of these pre-formed curves function by anchoring the catheter against an opposing wall within a patient's vasculature or other anatomy. Proper anchoring is often achieved by matching the predisposed shape of the catheter with the general shape of the targeted site. Often a curve is imparted to the distal end of a catheter with the intention of placing the catheter's distal opening at a desired location in the vessel, or alternatively, on the vessel wall. A guide catheter especially designed for a procedure in a coronary artery, for example, is shaped such that when the guide catheter is inserted into the femoral artery and through the aorta of a patient, the curvature of the catheter will place its distal tip inside one of the coronary ostia. Thus, a guide catheter for the right coronary artery is shaped differently than one for the left coronary artery. A guide catheter designed to provide access to a carotid artery is again shaped differently. Likewise, guide catheters of still other shapes are designed for other bodily passages and regions of interest. Further, there are differences between patients' body structures which require varying sizes of each curve type.

Guide catheters currently available from manufacturers are designed in a variety of shapes specific for different bodily passages and procedures. Those of skill in the art recognize these different shapes by names such as Judkins Right, Judkins Left, Amplatz Right, Amplatz Left, Bentson, Shepherd Hook, Cobra, Headhunter, Sidewinder, Newton, Sones and others, each formed in a different shape. Most of these different shapes are manufactured in gradations of size and/or curvature to accommodate differences among individual patients.

When a guide catheter is inserted and advanced within a patient, its pre-formed curved shape is often distorted by the tortuous vasculature and connecting passages of a patient's vasculature. The bends must essentially become straight as the catheter is slowly advanced within the anatomy, usually over a guidewire. In order for the pre-formed manufactured curves or bends to be effective in properly seating the guide catheter, however, the imparted curves must be capable of returning their pre-formed shape or at least a predictable variant of the original shape. This is referred to herein as curve retention. Similarly, after the guide catheter is properly seated, the curves of the catheter must retain the catheter's positioning despite the constant movements in response to normal bodily functions such as breathing or a heartbeat or when other devices are passed through the lumen of the positioned catheter.

Manufacturers, therefore, often add filler material, or alternatively, use stiffer materials in curved regions to increase curve retention. Although adding materials achieves better curve retention upon placement, decreasing the catheter's flexibility in curved regions causes significant alterations in the catheter's overall performance. Specifically, the catheter's trackability is often affected. For guide catheters having curves imparted within the distal regions of the catheter, the effect in trackability performance can be quite significant. Thus, it is a goal of the present invention to create a catheter design having exceptional curve retention without diminishing the catheter's flexibility and overall trackability performance.

SUMMARY OF THE INVENTION

The present invention provides a polymeric treatment for curved regions in shaft assemblies that increases curve retention without significantly affecting the flexibility within these regions. More specifically, the method of the present invention modifies the underlying crystalline morphology of a polymer in order to decrease crystal fracturing. In particular, the present invention treats polymeric materials suitable for catheter construction with a nucleating agent. A nucleating agent is a material that affects the number and size of crystals formed during the nucleation process. Nucleating agents introduce more nuclei into a polymer's nucleation process. Therefore, under similar cooling procedures, a polymer treated with a nucleating agent results in a rise in the number of crystals formed and a reduction in the overall size of each crystal when compared with an untreated polymer.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DETAILED DESCRIPTION OF THE PREFERRED EMBODIMENTS

The following detailed description should be read with reference to the drawings, in which like elements in different drawings are numbered identically. The drawings, which are not necessarily to scale, depict selected embodiments and are not intended to limit the scope of the invention. Examples of construction, materials, dimensions, and manufacturing processes are provided for selected elements. All other elements employ that which is known to those skilled in the field of the invention. Those skilled in the art will recognize that many of the examples provided have suitable alternatives that may be utilized.

Figure 1:
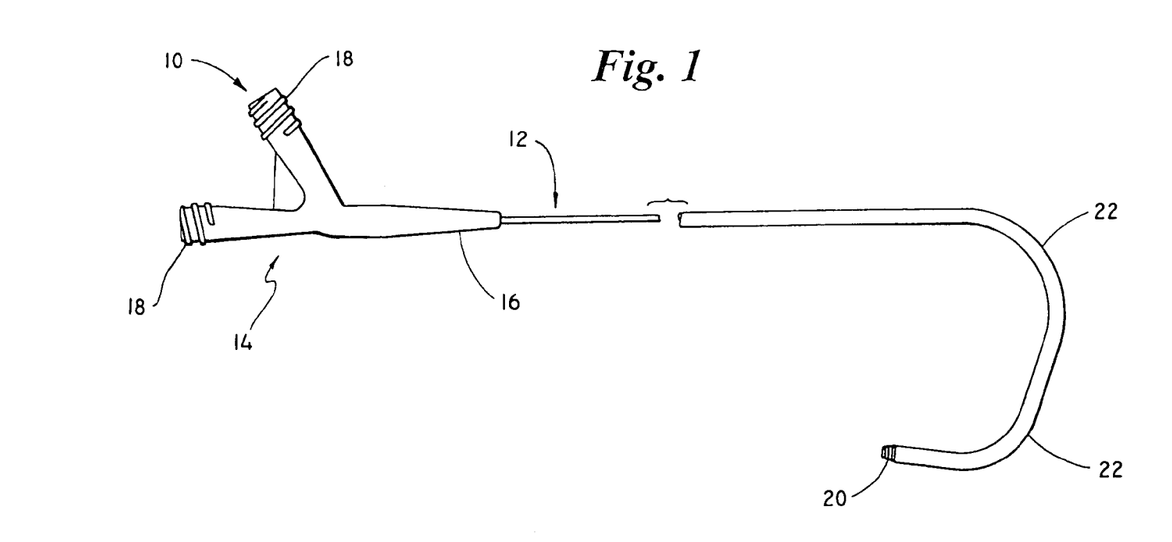
FIG. 1 is a partial plan view of a catheter assembly in accordance with the present invention.

Referring now to the drawings, FIG. 1 is a partial plan view of a catheter in accordance with the present invention. The catheter of the present invention may be used in conjunction with most catheter devices suited for placement within the human anatomy. As such, the catheter assembly may be utilized in cardiology, neurology, urology and gastroenterology, among others. In gastroenterological devices, the catheter of the present invention may be incorporated into the shaft design of an endoscope, or alternatively, into a biliary catheter. Likewise, in vascular devices, the catheter assembly 10 of the present invention may be incorporated into the shaft design of a guide or diagnostic catheter, or in the alternative, into the vascular catheters used to ultimately treat the maladies requiring the medical procedure.

For illustrative purposes, the catheter 10 is shown as a guide or diagnostic catheter, which is representative of a catheter that can incorporate the present invention. Other intravascular catheter embodiments are additionally suitable without deviating from the spirit and scope of the present invention.

The guide catheter 10 includes a shaft assembly 12. A conventional manifold assembly 14 is connected to the proximal end of the shaft assembly 12. The proximal end of the shaft assembly 12 attaches to a strain relief 16 that further extends into the manifold assembly 14. The strain relief 16 is generally made of a polyurethane material that snap-fits into the manifold assembly 14 at one end. The other end of the strain relief 16 is generally adhesively bonded to the shaft assembly 12, forming a continuous and sealed fluid connection from the proximal end of the manifold assembly 14 to the distal end of the shaft assembly 12.

A single manifold port 18 or multiple manifold ports 18 as shown in FIG. 1 extend from the manifold assembly 14 for attaching and fluidly connecting ancillary apparatus to a lumen extending through the guide catheter. Each manifold port 18 includes a lumen terminating into either a common lumen or a dedicated lumen extending within the shaft assembly 12 (e.g., a guidewire lumen). Functionally, the manifold assembly 14 additionally provides a convenient place for a physician to apply longitudinal or rotational forces in order to manipulate the guide catheter during a medical procedure.

The dimensions and materials used in making the shaft assembly 12 are selected based upon the desired catheter application. For instance, a guide catheter 10 is generally characterized as having a multi-layer tubular member construction. This tubular member includes at least a single lumen extending the length of the shaft assembly 12. The lumen within the guide catheter 10 possesses an inner diameter capable of receiving another catheter, preferably a diagnostic catheter. Since many diagnostic catheters have outer diameters in the range of 5 F–10 F, a guide catheter must either accommodate the largest diagnostic catheter, or identify those catheter sizes the guide catheter 10 may receive. The dimensions of guide catheters are well known in the art.

Materials used to form the guide catheter 10 vary depending upon the stiffness desired for the shaft assembly 12. Nylon and similar polyamides such as DURETHAN® (available from Bayer) are particularly suitable for rigid tubular members. Other suitable materials for a rigid tubular member include polyetheretherketone (PEEK), polyimide (PI), and polyetherimide (PEI). Rigidity may additionally be imparted to the tubular member by incorporating a braid on or within the tubular member. Polyether block amide (PEBA), in contrast to the rigid polyamides, is a relatively flexible polymeric material having a durometer of approximately 70 D. Finally, the use of a polyamide such as CRISTAMID® (available from Elf Atochem) imparts a slightly less rigid durometer than the rigid polyamides and slightly greater than the flexible PEBA material.

Disposed upon the distal end of the guide catheter 10 is a distal tip 20. The distal tip 20 generally comprises a soft polymeric material that allows the guide catheter 10 to navigate and traverse the tortuous pathways of a patient's vasculature in a manner as atraumatic as possible. Materials suitable for the distal tip 20 include a polyethylene, polyamide, or block copolymer such as PEBAX® having a lower durometer than the proximal shaft materials. In preferred embodiments, a distal tip 20 comprising a polymeric material having a durometer of about 28 D is heat welded or bonded to the distal end of the tubular member. In an alternative embodiment, the last ½ to 1 mm of the tip at its distal end is made of a different material from the tip material to form a tip extension. In particular, the last ½ to 1 mm is made from a material that is more durable relative to the softer tip material. In particular, the more durable material will resist deforming or tearing when in use, such as in tracking the patient's tortuous anatomy. For example, this last ½ mm to 1 mm may be manufactured from Marlex high-density polyethylene having approximately a 63 D durometer. This distal tip 20 material selection often improves the integrity of the tip region at its distal-most end.

In yet other embodiments, the distal tip 20 is molded to aid in catheter navigation, or alternatively, in a manner that more securely engages the distal tip 20 with a targeted site within the patient's anatomy. Distally tapering a distal tip 20 from a larger outer diameter to a smaller outer diameter enhances navigation of guide catheter 10. A smaller distal tip 20 allows the guide catheter 10 to more readily follow passages that are curved or branched.

As described in detail above, the stabilization of a guide catheter's position within a patient's anatomy is often achieved through curves or bends 22 imparted into the shaft assembly by the manufacturer. These pre-formed curves 22 act by anchoring a selected portion of the shaft assembly 12 against an opposing wall within a patient's vasculature or other body portion. Proper anchoring is often achieved by matching the predisposed shape of the curved shaft assembly 12 with the general curved anatomical shape around a targeted site. In vascular procedures involving treatment to one of the coronary arteries, often a curve 22 is imparted to the distal end of a shaft assembly 12 with the intention of placing the catheter's distal tip 20 at a desired angle. A guide catheter 10 especially designed for a procedure in a coronary artery, for example, has a shaft assembly 12 shaped so that when the guide catheter 10 is inserted through the aorta of the patient, the curvature of the catheter's shaft assembly 12 will place its distal tip 20 at an angle that engages one of the coronary ostia.

Guide catheters currently include a variety of shapes specific for different bodily passages and procedures. Those of skill in the art recognize these different shapes by names such as Judkins Right, Judkins Left, Amplatz Right, Amplatz Left, Bentson, Shepherd Hook, Cobra, Headhunter, Sidewinder, Newton, Sones and others, each formed in a different shape. The guide catheter 10 of FIG. 1 generally depicts a curve. Although one selected curve is shown in detail, additional pre-formed curves and bends, being known in the art, and including those listed above, are also incorporated as within the scope of the present invention. In order to understand how pre-formed curves and bends 22 are imparted to a guide catheter 10, and more specifically, how those bends 22 retain their shape, it is important to understand the physical characteristics of the polymers forming the curves 22.

Figure 2A:
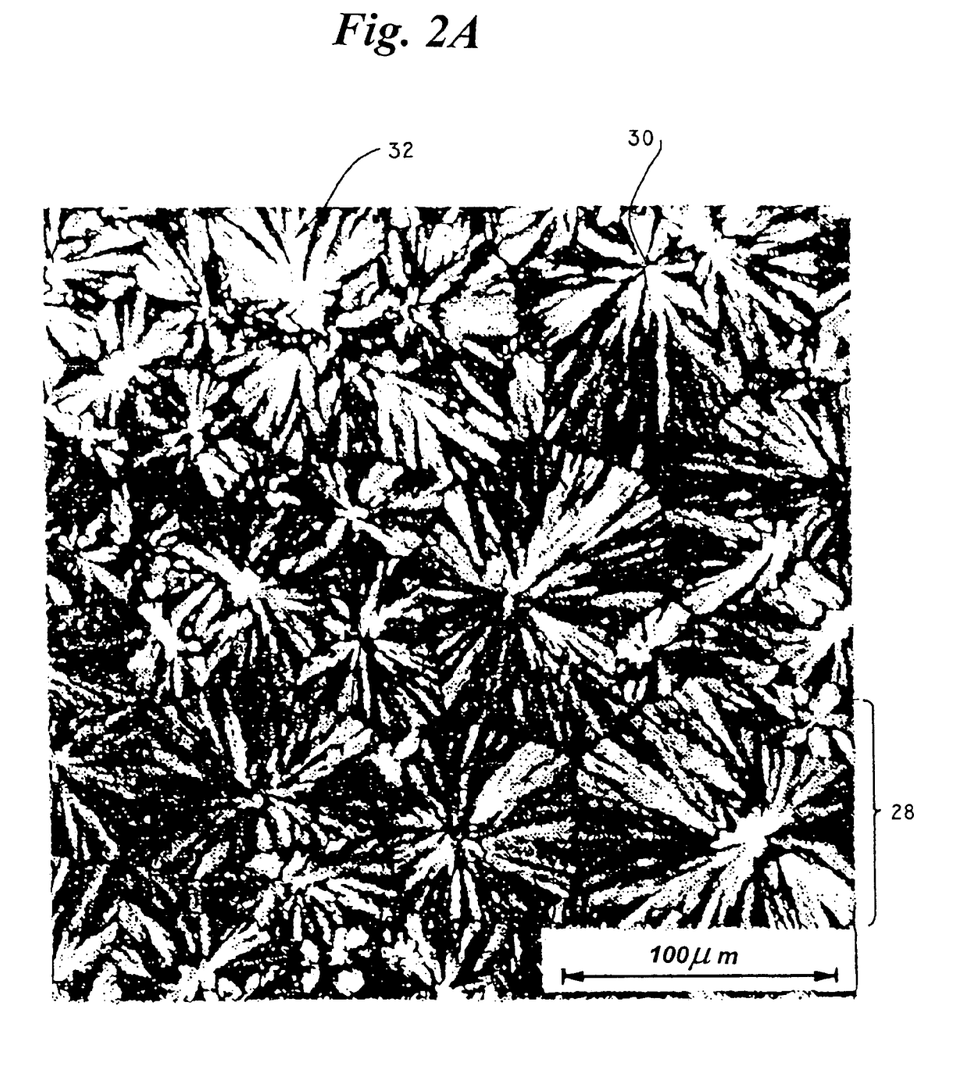
FIG. 2A is an illustration of the crystal morphology of a polymeric material lacking nucleating agent treatment.

Certain polymeric materials possess a crystalline microstructure. A polymer's flexibility, tensile strength and hardness are all directly related to the makeup of that polymer's crystalline microstructure. In particular, these physical attributes are greatly influenced by how the crystalline microstructure was initially developed, under the nucleation process. Nucleation is the process by which crystals 28 are formed. The nucleation process starts through the introduction of a foreign substance that acts as a nucleus 30 for the developing crystal 28. Under normal reaction conditions, nuclei 30 used for the nucleation process are generally naturally occurring impurities in the polymeric material itself. The first beginnings of a crystal 28 form on these nuclei 30. Once started, these crystals 28 quickly propagate into larger crystals by accretion. FIG. 2A illustrates the crystal 28 morphology of a typical polymeric material suitable for the present invention. The Figure depicts numerous individual crystals 28 each having a nucleus 30, and an array of fine grain structures 32 radiating from the nucleus 30.

The crystalline morphology of a polymeric catheter tubular member is developed after the tubular member is extruded. The molten polymeric material is shaped into a desired form and then cooled to retain that desired shape. During the cooling process, and more generally during the nucleation process, the crystals 28 propagate to support the desired shapen framework. The completion of the nucleation and cooling process results in a crystalline microstructure not unlike that depicted in FIG. 2A.

For some polymers, the nucleation process is very fast, and for other polymers, the process is so slow that the polymer generally retains an amorphous morphology. Thus, a key to understanding a polymer's crystalline microstructure, and later in manipulating that microstructure, is through quantifying the polymer's crystal growth rate. The crystal growth rate for any particular polymer is influenced by the polymer's nucleus density, the growth rate of crystals 28 in the polymer and the degree of cooling of the polymer melt. Materials suitable for forming the shaft assembly 12 of the present invention (PEEK, PI, PEI, PEBA and certain polyamides) all possess crystal growth rates that support a crystalline morphology. Moreover, these materials are quantified as having crystal growth rates that permit their crystalline microstructure to be modified during the nucleation process.

Modification of the crystalline microstructure is desirable in order to overcome some shortcomings in traditional manufacturing processes. Specifically, it is desirable to modify the crystalline microstructure in guide catheters 10 having pre-formed bends and curves 22. Under typical manufacturing processes, crystals 28 develop large elongated fine grain structures 32 that radiate from the crystal's nucleus 30. The relative size of crystals 28 makes them prone to fracturing along their elongated fine grain structures 32. Consequently, fracturing of the elongated fine grain structures 32 cause the polymeric material, as a whole, to lose retention in its imparted shape. Crystal fracturing is a particular problem in curved areas 22 of a guide catheter 10 where curve retention is paramount to stabilizing the guide catheter's position within a patient's anatomy.

When a guide catheter 10 is inserted and advanced within a patient, its pre-formed curved shape is distorted (essentially straightened) by the tortuous vasculature and connecting passages of a patient's vasculature. The bends 22 straighten as the guide catheter 10 is slowly advanced within the anatomy. Such unavoidable manipulations to the curved regions 22 of the guide catheter 10 cause the underlying crystalline microstructure to fracture. Once fractured, the guide catheter 10 is unable to retain its exact pre-formed shape or a predictable final shape. In order for the pre-formed manufactured curves 22 to be most effective in properly seating the guide catheter 10, however, the imparted curves 22 must be capable of retaining their pre-formed shape or a predictable final shape.

Current manufacturing processes compensate for the loss of curve retention by adding filler material, or alternatively, by using stiffer materials within the curved regions 22. Although these modifications increase curve retention, their addition also decreases the flexibility of guide catheter 10 within these curved regions 22. Moreover, a loss in flexibility within the curved regions 22 of the guide catheter 10 may also significantly alter the overall performance of guide catheter 10. Specifically, the guide catheter's trackability is often affected. For guide catheters 10 having curves 22 imparted within the distal regions of the guide catheter 10, the effect on trackability performance can be quite significant. The present invention provides a polymeric treatment for curved regions 22 in shaft assemblies that increases curve retention without affecting the flexibility within these regions.

The present invention modifies the underlying crystalline morphology of a polymer in order to decrease crystal fracturing. In particular, the present invention treats polymeric materials suitable for guide catheter 10 construction with a nucleating agent. A nucleating agent is a material that affects the number and size of crystals formed during the nucleation process.

Figure 2B:
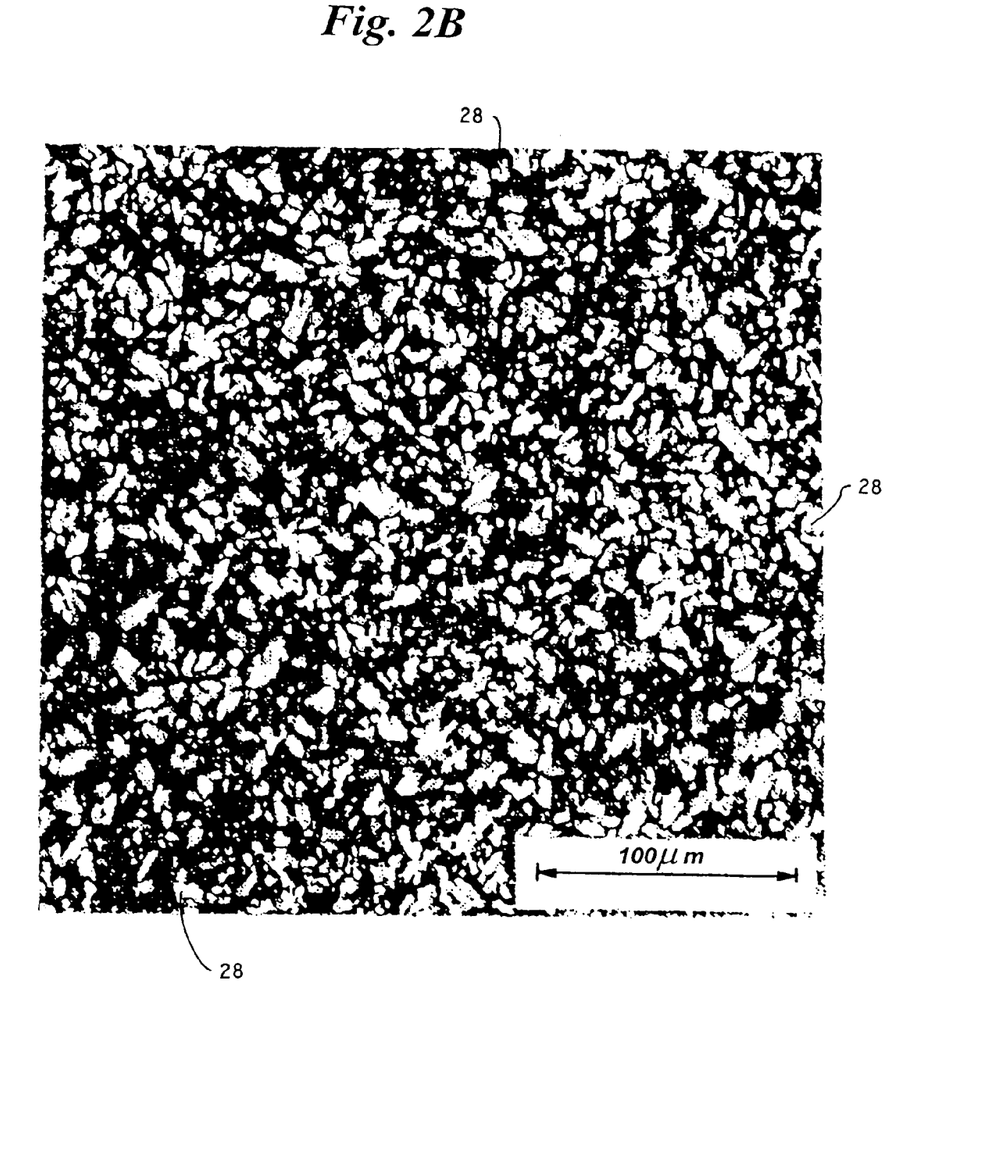
FIG. 2B is an illustration of the crystal morphology of the same polymeric material as shown in FIG. 2A, having been treated with a nucleating agent.

FIG. 2B depicts the same polymeric material shown in FIG. 2A. However, the material in FIG. 2B has been treated with a nucleating agent. Nucleating agents introduce more nuclei into a polymer's nucleation process. Therefore, under similar cooling procedures, a polymer treated with a nucleating agent results in an increase in the number of crystals 28 formed and a reduction in the overall size of each crystal 28, when compared with an untreated polymer under the same conditions. The discrepancy in crystal 28 number and size is best illustrated by comparing FIG. 2A (untreated) with FIG. 2B (treated with nucleating agents).

As described above, crystal fracturing occurs along the elongated fine grain structures 32 of the crystal 28. With nucleating agent treated polymers, however, the fine grain structures 32 are not highly elongated. Individual crystals 28 are highly crowded in nucleating agent treated polymers. As a result, crystal growth accretion is extremely short before a crystal 28 abuts a neighboring crystal 28. Thus, the elongated fine grain structures 32 are also very short. It is these shorter fine grain structures 32 that resist fracturing as a result of stresses applied to the crystalline framework.

Longer elongated fine grain structures 32 (seen in FIG. 2A) are more susceptible to fracturing because individual crystals 28 become weaker with increased size. Shorter elongated fine grain structures 32 (which cannot be fully illustrated due to the compact size of each crystal in FIG. 2B) are unlikely to fracture because of their compact size. This resistance to fracturing makes nucleated polymers particularly useful in the bends and curves of a catheter. In particular, such treated curves and bends fail to deform from their originally imparted configuration when advanced through a patient's anatomy. Moreover, these bends and curves are also more likely to retain their positioning within a patient's anatomy despite constant movements in response to normal bodily functions such as breathing and heartbeat. These attributes instill physician and patient confidence, alike, when using highly predictable guide catheters. The physician may feel comfortable that the angle imparted outside of a patient will be reproduced and be retained when the guide catheter 10 is inserted within the patient at the targeted site.

A number of nucleating agents suitable for shaft assembly 12 construction are commercially available. In a presently preferred embodiment, inorganic additives, organic additives and polymers are preferred nucleating agents. Examples of inorganic additives include, but are not limited to, talc, silica, kaolin, molybdenum disulfide, iron sulfide, titanium dioxide and sodium phenylphosphonate. Examples of organic additives include, but are not limited, to sodium p-tert-butylbenzoate, monton wax, montanic ester salts, salts of monocarboxylic acids and polycarboxylic acids. Examples of polymers include, but are not limited to, ethylene and acrylic ester copolymers, fumeric acid polymers, ethylene, propylene 1,4-hexadiene and norbornadiene. These nucleating agents possess superior nucleation rates for materials suitable for forming the guide catheter 10. More specifically, these nucleating agents are particularly suitable for polymeric materials used to form the pre-formed bends and curves 22 of particular catheter assembly embodiments. Utilization of additional nucleating agents suitable for the preferred polymeric materials listed above, being known in the art, is also incorporated as within the scope of the present invention.

Nucleating agents are commercially available in a variety of differing material states. For example, specific nucleating agents are commercially available as powders, pastes and liquids. The use of one material state may be more appropriate than another depending upon the manner of manufacturing of the resulting catheter device. Nucleating agents in powder form are particularly suited for incorporation within a polymeric material. The powdered nucleating agent is measured, added and dispersed within the polymeric material to maintain a specified concentration throughout the mixture. The required ratio of nucleating agent to polymer that initiates the desired change in crystalline morphology may vary depending upon the specific polymeric material used. In certain polymeric materials, any further increases in the required concentration ratio fail to further improve the crystalline microstructure of the polymer. In some embodiments, the ratio of nucleating agent to polymer is about 0.5% to about 99.5% by weight. In preferred embodiments, the nucleating agent is present in a concentration of about 0.01% to about 1.0% by weight.

Once the nucleating agent containing polymer is properly admixed, the polymeric mixture is then fed into an extruder. The extruder then dispenses the admixed polymeric material to form a tubular member, and this member is configured to a desired shape. Nucleating agents in paste and liquid form are additionally suitable for this manufacturing method. Alternatively, the desired shape can be formed in a subsequent heat treatment process wherein a select portion including a curve is melted and re-crystallized in a desired configuration.

As discussed above, the catheter assembly of the present invention may also be incorporated into other catheters. Specifically, the multi-lumen shaft assemblies of balloon dilatation catheters 40 are suited for the catheter assembly improvement of the present invention. The basic construction and use of multi-lumen balloon dilatation catheters 40 are all well known in the art. An example of an OTW catheter may be found in commonly assigned U.S. Pat. No. 5,047,045 to Arney et al. An example of an SOE catheter is disclosed in commonly assigned U.S. Pat. No. 5,156,594 to Keith.

Multi-lumen catheter 40 construction generally includes the use of an inner tubular member 42 and an outer tubular member 44. In one embodiment, the spatial orientation of the two tubular members is such that the outer tubular member 44 is coaxially displaced over the inner tubular member 42 defining an annular inflation lumen therebetween. This spatial relationship is best illustrated with reference to FIG. 3.

Figure 3:
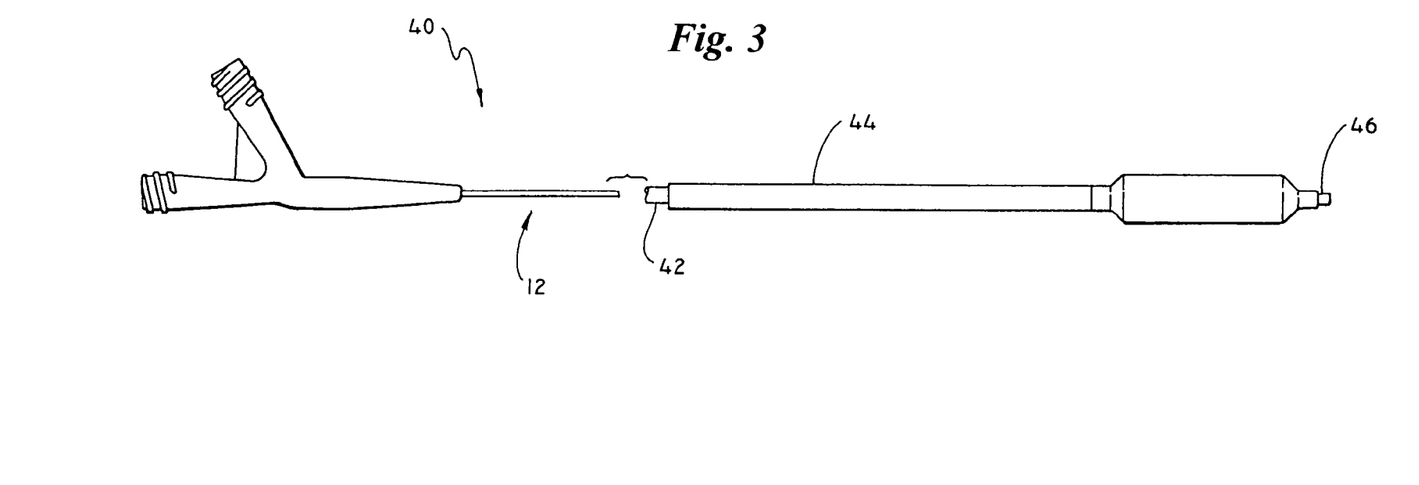
FIG. 3 is partial plan view of a diagnostic catheter assembly in accordance with the present invention.

Materials used to form the outer tubular member may vary upon the stiffness desired for the shaft assembly 12. Nylon and similar polyamides such as DURETHAN® (available from Bayer) are particularly suitable for rigid outer tubular member 44. Other suitable materials for a rigid outer tubular member 44 include polyetheretherketone (PEEK), polyimide (PI), and polyetherimide (PEI). Polyether block amide (PEBA), in contrast to the rigid polyamides, is a relatively flexible polymeric material having a durometer of approximately 70 D. Finally, the use of a polyamide such as CRISTAMID® (available from Elf Atochem) imparts a slightly less rigid durometer than the rigid polyamides and slightly greater than the flexible PEBA material. All of these materials possess crystal growth rates that support a crystalline morphology. Moreover, these materials are quantified as having crystal growth rates that permit their crystalline microstructure to be modified during the nucleation process.

The inner tubular member 42 defines a guidewire lumen, which provides a passage for a guidewire 46. The inner tubular member 42 is generally made of polyethylene such as Marlex HDPE. In alternative embodiments, the inner tubular member is made of, or lined with, a lubricious material such as polytetrafluoroethylene (PTFE). Materials suitable for forming the inner tubular member 42 are generally classified as having a rapid crystallization growth rate. In contrast to materials forming the outer tubular member 44, materials forming the inner tubular member 42 generally possess such rapid crystal growth rates that they fail to support a crystalline morphology that may be modified using nucleating agents.

The benefits of modifying the outer tubular member 44 may be transferred to the inner tubular member 42, and thereby, to the balloon dilatation catheter 40 as a whole. Because of the spatial relationship within the multi-lumen catheter assembly, the outer tubular member 44 restrains the inner tubular member 42. Therefore, modifying the outer polymeric structure of tubular member 44, in effect, also modifies the performance characteristics experienced by the inner tubular member 42. Nucleating agent modifications to the outer tubular member 44 are similar to those with reference to the guide catheter assembly 10 of FIG. 1.

Numerous characteristics and advantages of the invention covered by this document have been set forth in the foregoing description. It will be understood, however, that this disclosure is, in many respects, only illustrative. Changes may be made in details, particularly in matters of shape, size and ordering of steps without exceeding the scope of the invention. The invention's scope is of course defined in the language in which the appended claims are expressed.

What is claimed is:

1. A catheter shaft comprising:
   an outer tubular member including a polymeric material, the outer tubular member having a proximal end, a distal end, a length and a lumen extending therethrough, wherein the outer tubular member includes a pre-formed bend along a portion of the length of the outer tubular member, wherein the polymeric material forming at least a portion of the pre-formed bend includes a sufficient quantity of a nucleating agent dispersed therein to provide an altered crystalline microstructure within at least a portion of the pre-formed bend; and
   an inner tubular member disposed within the lumen of the outer tubular member, the inner tubular member including a polymeric material having a substantially unaltered crystalline microstructure over its length.

2. The catheter of claim 1, wherein the crystalline microstructure of the polymeric material of the inner tubular member is substantially unaltered during a crystallization process.

3. The catheter of claim 1, wherein the polymeric material of the inner tubular member has a rapid crystalline growth rate.

4. The catheter of claim 1, wherein the polymeric material of the outer tubular member is selected from the group consisting of polyamide, polyethylene terephthalate, polyetheretherketone, polyimide, polyetherimide and polyether block amide and mixtures thereof.

5. The catheter of claim 1, wherein the polymeric material of the inner tubular member includes a polyethylene, a polytetrafluoroethylene, or a mixture thereof.

6. The catheter of claim 1, wherein the nucleating agent is present in a concentration of about 0.01% to 1.0% by weight.

7. The catheter shaft of claim 1, wherein the catheter shaft is a portion of a guide catheter.

8. The catheter shaft of claim 1, wherein the catheter shaft is a portion of a vascular catheter.

9. The catheter shaft of claim 1, wherein the catheter shaft is a portion of a biliary catheter.

10. A catheter shaft comprising:
    an outer tubular member having a proximal end, a distal end, a length and a lumen extending therethrough, wherein the outer tubular member includes a polymeric material having a crystalline microstructure, the polymeric material having a sufficient quantity of a nucleating agent dispersed therein to modify the crystalline microstrucrure during a nucleation process; and
    an inner tubular member disposed within the lumen of the outer tubular member and extending at least a portion of the length of the outer tubular member, wherein the inner tubular member includes a polymeric material having a crystalline microstructure which fails to support a crystalline morphology that may be modified using a nucleating agent;
    wherein the outer tubular member includes a pre-formed bend along a portion of the length of the outer tubular member, the sufficient quantity of the nucleating agent dispersed at least at the pre-formed bend.

11. The catheter shaft of claim 10, wherein the polymeric material of the inner tubular member has a rapid crystalline growth rate.

12. The catheter shaft of claim 10, wherein the polymeric material of the outer tubular member is selected from the group consisting of polyamide, polyethylene terephthalate, polyetheretherketone, polyimide, polyetherimide and polyether block amide and mixtures thereof.

13. The catheter shaft of claim 10, wherein the polymeric material of the inner tubular member includes a polyethylene, a polytetrafluoroethylene, or a mixture thereof.

14. The catheter shaft of claim 10, wherein the nucleating agent is present in a concentration of about 0.01% to 1.0% by weight.

15. A catheter shaft comprising:
    an outer tubular member having a proximal end, a distal end and a lumen extending therethrough, wherein at least a portion of the outer tubular member includes a polymeric material having a crystalline microstructure, wherein the polymeric material includes a sufficient quantity of a nucleating agent to alter the crystalline microstructure of the polymeric material; and an inner tubular member disposed within the lumen of the outer tubular member, the inner tubular member including a polymeric material having a crystalline microstructure having a rapid crystallization growth rate;

wherein the outer tubular member includes a pre-formed bend along a portion of the outer tubular member, the sufficient quantity of the nucleating agent dispersed at least at the pre-formed bend.

16. The catheter shalt of claim 15, wherein the crystalline microstructure of the polymeric material of the inner tubular member is substantially unaltered during a crystallization process.

17. The catheter shall of claim 16, wherein the crystallization process includes the use of a nucleating agent.

18. The catheter shaft of claim 15, wherein the polymeric material of the outer tubular member is selected from the group consisting of polyamide, polyethylene terephthalate, polyetheretherketone, polyimide, polyetherimide and polyether block amide and mixtures thereof.

19. The catheter shaft of claim 15, wherein the polymeric material of the inner tubular member includes a polyethylene, a polytetrafluoroethylene, or a mixture thereof.

20. The catheter shaft of claim 15, wherein the nucleating agent is present in a concentration of about 0.01% to 1.0% by weight.

21. A catheter shaft including a pre-formed curve portion, the catheter shaft comprising:

an outer tubular member having a proximal end, a distal end, and a lumen extending therethrough, the outer tubular member at least extending throughout the pineformed curve portion of the catheter shaft; and an inner tubular member coaxially positioned within the lumen of the outer tubular member and defining an annular inflation lumen therebetween;

wherein at least a portion of the outer tubular member extending throughout the pre-formed curve portion of the catheter shaft comprises a polymeric material including a sufficient quantity of a nucleating agent dispersed therein to increase the nucleus density of the polymeric material in order to improve the curve retention of the pre-formed curve portion of the catheter shaft.

22. A catheter comprising:

an elongate shaft having a proximal end and a distal end, the elongate shaft including a first pre-formed bend section intermediate the proximal end and the distal end, and a second pre-formed bend section intermediate the proximal end and the distal end, the first pre-formed bend section of the elongate shaft comprising:

(a) an outer tubular member comprising a polymeric material including a sufficient quantity of a nucleating agent dispersed therein to increase the nucleus density of the polymeric material in order to improve the curve retention of the first pre-formed bend section of the elongate shaft; and (b) an inner tubular member positioned within the outer tubular member.

23. The catheter of claim 22, wherein the second pre-formed bend section of the elongate shaft comprises:

(a) the outer tubular member comprising a polymeric material including a sufficient quantity of a nucleating agent dispersed therein to increase the nucleus density of the polymeric material in order to improve the curve retention of the second pre-formed bend section of the elongate shaft; and (b) the inner tubular member positioned within the outer tubular member.

24. The catheter of claim 23, wherein the inner tubular member is coaxially positioned within the outer tubular member, defining an inflation lumen therebetween.

* * * * *

UNITED STATES PATENT AND TRADEMARK OFFICE
CERTIFICATE OF CORRECTION

PATENT NO. : 7,128,956 B2
APPLICATION NO. : 10/983470
DATED : October 31, 2006
INVENTOR(S) : Bruce Yiqun Wang et al.

Page 1 of 1

It is certified that error appears in the above-identified patent and that said Letters Patent is hereby corrected as shown below:

Column 10
Line 36, delete "microstrucrure" and insert therefor -- microstructure --.

Column 11
Line 11, delete "shalt" and insert therefor -- shaft --.
Line 15, delete "shall" and insert therefor -- shaft --.
Lines 32-33, delete "pine-formed" and insert therefor -- pre-formed --.

Signed and Sealed this

Twentieth Day of February, 2007

JON W. DUDAS
*Director of the United States Patent and Trademark Office*